US006599536B1

(12) United States Patent
Kelly et al.

(10) Patent No.: US 6,599,536 B1
(45) Date of Patent: Jul. 29, 2003

(54) THERAPY OF ESTROGEN-ASSOCIATED DISORDERS

(75) Inventors: Graham Edmund Kelly, Northbridge (AU); Alan James Husband, McMahon's Point (AU)

(73) Assignee: Novogen Research Pty Ltd, New South Wales (AU)

( * ) Notice: Subject to any disclaimer, the term of this patent is extended or adjusted under 35 U.S.C. 154(b) by 0 days.

(21) Appl. No.: 09/647,092

(22) PCT Filed: Mar. 26, 1999

(86) PCT No.: PCT/AU99/00222

§ 371 (c)(1),
(2), (4) Date: Dec. 5, 2000

(87) PCT Pub. No.: WO99/48496

PCT Pub. Date: Sep. 30, 1999

(30) Foreign Application Priority Data

Mar. 26, 1998 (AU) .............................................. PP2607

(51) Int. Cl.[7] .............................................. A61K 35/78
(52) U.S. Cl. ...................................... 424/725; 424/757
(58) Field of Search .............................. 424/195.1, 725, 424/757

(56) References Cited

U.S. PATENT DOCUMENTS

| 3,471,520 A | 10/1969 | Irmscher et al. |
| 3,535,344 A | 10/1970 | Irmscher et al. |
| 3,973,608 A | 8/1976 | Umezawa et al. |
| 4,200,692 A | 4/1980 | Puls et al. |
| 4,264,509 A | 4/1981 | Zilliken |
| 4,301,251 A | 11/1981 | Rumyantseva et al. |
| 4,366,082 A | 12/1982 | Zilliken |
| 4,390,559 A | 6/1983 | Zilliken |
| 5,141,746 A | 8/1992 | Fleury et al. |
| 5,320,949 A | 6/1994 | Shen |
| 5,352,384 A | 10/1994 | Shen |
| 5,424,331 A | 6/1995 | Shlyankevich |
| 5,498,631 A | 3/1996 | Gorbach et al. |
| 5,506,211 A | 4/1996 | Barnes et al. |
| 5,516,528 A | 5/1996 | Hughes et al. |
| 5,530,112 A | 6/1996 | Greenshields et al. |
| 5,547,866 A | 8/1996 | Durzan et al. |
| 5,554,519 A | 9/1996 | Weber et al. |
| 5,569,459 A | 10/1996 | Shlyankevich |
| 5,637,561 A | 6/1997 | Shen et al. |
| 5,679,806 A | 10/1997 | Zheng et al. |
| 5,700,669 A | 12/1997 | Hanson et al. |
| 5,498,631 A | 3/1998 | Gorbach et al. |
| 5,726,034 A | 3/1998 | Bryan et al. |
| 5,733,926 A | 3/1998 | Gorbach |
| 5,763,389 A | 6/1998 | Shen et al. |
| 5,789,581 A | 8/1998 | Matsuura et al. |
| 5,792,503 A | 8/1998 | Gugger et al. |
| 5,830,887 A | 11/1998 | Kelly |
| 5,942,539 A | 8/1999 | Hughes, Jr. et al. |
| 6,004,558 A | 12/1999 | Thurn et al. |
| 6,146,668 A | 11/2000 | Kelly et al. |
| 6,340,703 B1 | 1/2002 | Kelly |
| 6,497,906 B1 | 12/2002 | Kelly |
| 2002/0035074 A1 | 3/2002 | Kelly |

FOREIGN PATENT DOCUMENTS

| AU | A-24813/97 | 12/1997 |
| EP | 0129667 A1 | 1/1985 |
| EP | 0135172 A2 | 3/1985 |
| EP | 0136569 A2 | 4/1985 |
| EP | 0426998 A2 | 5/1991 |
| EP | 0 906 761 A2 | 4/1999 |
| GB | 1482238 | 8/1977 |
| JP | 61246124 A | 11/1986 |
| JP | 62106016 A | 5/1987 |
| JP | 62106017 | 5/1987 |
| JP | 62126186 A | 6/1987 |
| JP | 1042427 A | 2/1989 |
| JP | 01258669 A | 10/1989 |
| JP | 1258669 A | 10/1989 |
| JP | 02067218 A | 3/1990 |
| JP | 02069165 A | 3/1990 |
| JP | 2160722 A | 6/1990 |
| JP | 03047049 A | 2/1991 |
| WO | WO 93/23069 | 11/1993 |
| WO | WO 94/23716 | 10/1994 |
| WO | WO 98/08503 | 3/1998 |
| WO | WO 98/48790 | 11/1998 |
| WO | WO 98/49153 | 11/1998 |
| WO | WO 98/52546 | 11/1998 |
| WO | WO 98/56373 | 12/1998 |
| WO | WO 99/18927 A1 | 4/1999 |
| WO | WO 00/03707 | 1/2000 |

OTHER PUBLICATIONS

Wang et al. Phytoestrogen Concentration Determines Effects on DNA Synthesis in Human Breast Cancer Cells; Nutrition and Cancer, 28(3), pp. 236–247, 1997.*

Kelly et al., "Metabolites of dietary (soya) isoflavones in human urine," Clinica Chimica Acta 223(1–2), pp. 9–22 (Dec. 31, 1993).

(List continued on next page.)

Primary Examiner—Christopher R. Tate
Assistant Examiner—Patricia D Patten
(74) Attorney, Agent, or Firm—Finnegan, Henderson, Farabow, Garrett & Dunner, LLP

(57) ABSTRACT

A method for the treatment, prophylaxis, amelioration or prevention of disorders associated with abnormally high activity of steroidal estrogens, which includes administering to a human subject a composition comprising an isoflavone-containing extract of clover or chick peas, said extract comprising primarily biochanin, or a ratio of biochanin to one or more of the isoflavones from the group formononetin, daidzein and genistein in the range of from about 2:1 to about 5:1, optionally in association with one or more pharmaceutically acceptable carriers, excipients, auxiliaries and/or diluents is described. Also described are compositions and uses comprising the isoflavone containing extracts.

9 Claims, No Drawings

OTHER PUBLICATIONS

Mazur et al.; "Natural and anthropogenic environmental oestrogens: the scientific basis for risk assessment*—Naturally occurring oestrogens in food," Pure & Appl. Chem. 70(9), pp. 1759–1776 (1998).

Mazur et al., "Isolfavonoids and lignans in legumes: Nutritional and health aspects in humans," Nutritional Biochemistry 9, pp. 193–200 (1998).

Schultz, "Isoflavonglucoside Formononetin–7–glucosid und Biochanin A–7–glucosid in *Trifolium pratense* L.," Die Naturwissenschaften, 52(18), p. 517, Sep. 1965, English Abstract.

Statutory Declaration of Joseph Nicolas Van Haaster, declared Jan. 26, 1999, including Exhibit "JNVH–1," 20 pages.

Statutory Declaration of Norbert Krause, declared Nov. 5, 1998, 23 pages.

Statutory Declaration of Hubert Regtop, declared Nov. 24, 1998, 53 pages.

Statutory Declaration of Kerry Martin Bone, declared Oct. 5, 1998, 31 pages.

Statutory Declaration of Nancy Beckham, declared Sep. 8, 1998, 20 pages.

Statutory Declaration of G. Clements, declared Jan. 27, 1999, 2 pages.

Statutory Declaration of Fiona Bathgate, declared Mar. 24, 1998, 4 pages.

Amended Statutory Declaration of Fiona Bathgate, declared Oct. 26, 1998, 2 pages.

Statutory Declaration of Julie Hill, declared Apr. 4, 1998, 2 pages.

Statutory Declaration of Ngaire Petit–Young, declared Nov. 5, 1998, 3 pages.

Statutory Declaration of Jennifer Caprinelli, declared Oct. 21, 1998, 2 pages.

Grunert E. and Woelke, G., "Isoflavone in einigen Weiβ–und Rotkleesorten und ihre oestrogene Wirksamkeit bei juvenilen Mäusen," Deutsche Tierärztliche Wochenschrift, 74. Jahrgang 1967, p. 431–433.

Lindner, H.R., "V/1 Occurrence of Anabolic Agents in Plants and their Importance," Environmental Quality and Safety Supplement, Thieme, Stuttgart, Germany, 1976, 5: 151–158.

Naim, M., "The Isolation, Characterization and Biological Activity of Isoflavones from Soybeans," Submitted to the Senate of the Hebrew University of Jerusalem—Oct. 1974.

Sharma, R.D., "Effect of Various Isoflavones on Lipid Levels in Triton–treated Rats", Atherosclerosis 33, 1979, p. 371–375.

Weinberg, David S. et al., "Identification and Quantification of Anticarcinogens in Garlic Extract and Licorice Root Extract Powder", Journal of High Resolution Chromatography, 1992, p. 641–654.

EPO Communication dated Mar. 8, 2002.

EPO Supplementary Partial European Search Report dated Oct. 11, 2002.

Walz, E., "Isoflavon– und Saponin–Glucoside in *Soja hispida*," Justus Liebigs Annalen der Chemie., vol. 489, pp. 118–155 (1931).

The Merck Index, $8^{th}$ Ed., "Daidzein," "Formononetin," and "Geinstein," pp. 320, 484, and 469–470 [respectively], (1968).

Y. Liu et al., Chemical Abstracts, vol. 115, No. 8: Abstract No. 78763p, p. 466 (1991).

Aldercreutz, H. et al., "Determination of Urinary Lignans and Phytoestrogen Metabolites, Potential Antiestrogens and Anticarcinogens, in Urine of Women on Various Habitual Diets," *J. steroid Biochem.*, vol. 25, No. 58, pp. 791–797 (1986).

Aldercreutz, H. et al., "Effect of Dietary Components, Including Lignans and Phytoestrogens, on Enterohepatic Circulation and Liver Metabolism of Estrogens and on Sex Hormone Binding Globulin (SHBG)," *J. steroid Biochem*, vol. 27, No. 4–6, pp. 1135–1144 (1987).

Aldercreutz, H. et al., "Dietary Phytoestrogens and Cancer: In Vitro and In Vivo Studies," *J. Steroid Biochem. Molec. Biol.*, vol. 41, No. 3–8, pp. 331–337 (1992).

Aldercreutz, H. et al., "Dietary phyto–oestrogens and the menopause in Japan," *The Lancet*, pp. 1233, (1992).

Aldercreutz, H. et al., "Excretion of the Lignans Exterolactone and Enterodiol and of Equol in Omnivorous and Vegetarian Postmenopausal Women and in Women with Breast Cancer," *The Lancet*, pp. 1295–1299, (1982).

Aldercreutz, H., "Lignans and Phytoestrogens", *Front. gastrointest. Res.*, vol. 14, pp. 165–176, (1988).

Aldercreutz, H. et al., "Urinary excretion of lignans and isoflavonoids phytoestrogens in Japanese men and women consuming a traditional Japanese diet," *Am. J. Clin. Nutr.*, vol. 54, pp. 1093–1100, (1991).

Aldercreutz, H., "Western diet and Western diseases: some hormonal and biochemical mechanisms and associations," *Scand. J. Clin. Lab. Invest*, Suppl. 201, pp. 3–23, (1990).

Akkad, Andrea A. et al., "Abnormal Uterine Bleeding on Hormone Replacement: The Importance of Intrauterine Structural Abnormalities," *Obstetrics & Gynecology*, vol. 86, pp. 330–334 (1995).

Anderson M.D., J. et al., "Meta–Analysis of the Effects of Soy Protein Intake on Serum Lipids," *New Eng. J. Med.*, vol. 333, No. 5, pp. 276–282, (1995).

Barnes, S. et al., "Soybeans Inhibit Mammary Tumors in Models of Breast Cancer," *Mutagens and Carcinogens in the Diet*, pp. 239–253, (1990).

Bailey, E.T. et al., "Isoflavone Concentrations in the Leaves of the Species of the Genus Trifolium, Section Calycomorphum," Aust. J. agric. Res., vol. 22, No. 5, pp. 731–736, (1971).

Bannwart, C. et al., "Identification of the isoflavonic phytoestrogen daidzein in human urine," *Clinica Chimica Acta*, vol. 136, pp. 165–172, (1984).

Barrow, N.J., "Nutrient Potential and Capacity," *Aust. J. Agric. Res.*, vol. 17, pp. 849–861, (1966).

Barrow, N.J. et al., "Nutrient Potential and Capacity", *Aust. J. Agric. Res.*, vol. 18, pp. 55–62, (1967).

Beck, A.B., "The Oestrogenic Isoflavones of Subterranean Clover," *Aust. J. Agric. Res.*, vol. 15, pp. 223–230, (1964).

Beckham, N., "Estrogenic Activity in Plants—Summary of Talk by Nancy Beckham," from the Brisbane Seminar, 2 pgs., Jan., 1985.

Beckham, N., "Menopause," *The Family Guide to Natural Therapies*, Greenhouse Publications, Richmond, pp. 41–42, and 50, (1988).

Beckham, N., "Herbal Help to Avoid Menopause Symptoms," *Australian Wellbeing*, No. 29, pp. 74–76, (1988).

Beckham, N., "Phyto–oestrogens and Comounds (sic) that Affect Oestrogen Metabolism—Part I," *Aust. J. Med. Herbalism*, vol. 7, No. 1, pp. 11–16, (1995).

Beckham, N., "Phyto–oestrogens and Compounds that Affect Oestrogen Metabolism—Part II," *Aust. J. Med. Herbalism*, vol. 7, No. 2, pp. 27–33, (1995).

Bennetts, H.W. et al., "A Specific Breeding Problem of Sheep on Subterranean Clover Pastures in Western Australia," *The Australian Veterinary Journal*, vol. 22, pp. 2–12, (1946).

Beuker Velasse—Advertising Brochure—with English language translation.

Bombardelli, E., "Chapter 7: Technologies for the Processing of Medicinal Plants," in *The Medicinal Plant Industry*, R.O.B. Wijesekera (Ed.), CRC Press LLC, New York, NY, pp. 85–98, (1991).

Bradbury, R.B. et al., "The Chemistry of Subterranean Clover. Part I. Isolation of Formononetin and Genistein," *J. Chem. Soc.*, pp. 3447–3449, (1951).

Bradbury, R.B. et al., "Estrogens and Related Substances in Plants," in *Vitamins and Hormones: Advances in Research and Applications vol. XII*, R.S. Harris et al. (Eds.), pp. 207–233, (1954).

Brandi, M.L., "Flavonoids: biochemical effects and therapeutic applications," *Bone and Mineral*, vol. 19 (Suppl.), pp. S3–S14, (1992).

Braden, A.W.H. et al., "Comparison of Plasma Phyto–Oestrogen Levels in Sheep and Cattle After Feeding on Fresh Clover," *Aust. J. agric. Res.*, vol. 22, pp. 663–670, (1971).

Braden, A.W.H. et al., "The Oestrogenic Activity and Metabolism of Certain Isoflavones in Sheep," *Aust. J. Agric. Res.*, vol. 18, pp. 335–348, (1967).

Bradley, P.R. (Ed.), "Contents" and "Index," in *British Herbal Compendium, vol. 1: A handbook of scientific information on widely used plant drugs*, British Herbal Medicine Association, Bournemouth, Dorset, pp. 5, 231–239, (1992).

Buzzell, R.I. et al., "Inheritence of Flavonol Glycosides in Soybeans," *Can. J. Genet. Cytol.*, vol. 15, pp. 865–867, (1973).

Cassady, J.M. et al., Use of a Mammalian Cell Culture Benzo(a)pyrene Metabolism Assay for the Detection of Potential Anticarcinogens from Natural Products: Inhibition of Metabolism by Biochanin A, an Isoflavone from *Trifolium pratense* L, Cancer Research, vol. 48, pp. 6257–6261, (1998).

Circle, S. J. et al., "Processing Soy Flours, Protein Concentrates and Protein Isolates," in *Soybeans: Chemistry and Technology, vol. 1: Proteins*, A.K. Smith et al. (Eds.), Avi Publishing Company, Inc., Westport, CT, pp. 294–338, (1972).

Collins, B.M. et al., "The estrogenic and antiestrogenic activities of phytochemicals with the human estrogen receptor expressed in yeast," *Steroids*, vol. 62, pp. 365–372, (1997).

Coward, L. et al., "Genistein, Daidzein, and Their β–Glycoside Conjugates: Antitumor Isoflavones in Soybean Foods from American and Asian Diets," *J. Agric. Food Chem.*, vol. 41, pp. 1961–1967, (1993).

Culbreth, David M.R. (Ed.), *A Manual of Materia Medica and Pharmacology*, Eclectic Medical Publications, Portland, OR, pp. 19–22, (1922).

Davies, L.H. et al., "Further Studies on Oestrogenic Activity in Strains of Subterranean Clover (*Trifolium Subterraneum* L.) In South–Western Australia," *Aust. J. Agric. Res.* vol. 16, No. 6, pp. 937–950, (1965).

Davis, H. et al., "Extraction," *Bentley's Text–Book of Pharmaceuticals*, 6th ed., XVIII, pp. 272–273, (1956).

Dewick, P.M. et al., "Isoflavonoids,", *The Flavonoids: Advances in Research Since 1986*, Ed. by J. B. Harborne, Published by Chapman & Hall.

Düker, E. et al., "Effects of Extracts from *Cimicifuga racemosa* on Gonadotropin Release in Menopausal Women and Ovariectomized Rats," *Planta Med.*, vol. 57, pp. 420–424, (1991).

Eldridge, A.C., "Determination of Isoflavones in Soybean Flours, Protein Concentrates, and Isolates," *J. Agric. Food. Chem.*, vol. 30, No. 2, pp. 353–355, (1982).

Eldridge, A.C., "High–performance liquid chromatography separation of soybean isoflavones and their glucosides," *J. Chromatography*, vol. 234 pp. 494–496, (1982).

Eldridge, A.C. et al., "Soybean Isoflavones: Effect of Environment and Variety on Composition," *J. Agric. Food Chem.*, vol. 31 pp. 394–396, (1983).

Farmakalidis, E. et al., "Isolation of 6"–O–Acetylgenistin and 6"–O–Acetyldaidzin from Toasted Defatted Soyflakes," *J. Agric. Food Chem.*, vol. 33, pp. 385–389, (1985).

Farmakalidis, E. et al., "Semi–preparative high–performance liquid chromatographic isolation soybean isoflavones," *J. Chromatography*, vol. 295, pp. 510–514, (1984).

Farnsworth, N.R. et al., "Potential Value of Plants as Sources of New Antifertility Agents II," *J. Pharm. Science*, vol. 64, No. 5, pp. 717–753, (1975).

Francis, C.M. et al., "The Distribution of Oestrogenic Isoflavones in the Genus Trifolium," *Aust. J. Agric. Res.*, 18:47–54, (1967).

Francis, C.M. et al., "Varietal Variation in the Isoflavone Content of Subterranean Clover: Its Estimation by a Microtechnique," *Aust. J. Agric. Res.*, vol. 16, pp. 557–564, (1965).

Gaynor, J.D. et al., "HPLC Separation and Relative Quantification of Kaempferol Glycosides in Soybean," *Chromatographia*, vol. 25, No. 12, pp. 1049–1053, (1988).

Gildersleeve, R.R. et al., "Screening Rose Clover and Subterranean Clover Germplasm for Isoflavones," *Crop Sci.*, vol. 31, No. 5, pp. 1374–1376, (1991).

Gildersleeve, R.R. et al., "Detection of Isoflavones in Seedling Subterranean Clover," *Crop Sci.*, vol. 31, pp. 889–892, (1991).

Gladstones, J.S., "Naturalized Subterranean Clover Strains in Western Australia: A Preliminary Agronomic Examination," *Aust. J. agric. Res.*, vol. 18, pp. 713–731, (1967).

Goh, J.T.W. et al., "Postmenopausal Endometrioma and Hormonal Replacement Therapy," *Aust NZ J. Obstet Gynaecol*, vol. 32, pp. 384–385 (1992).

Grodstein, F., et al., "Postmenopausal Hormone Use and Cholecystectomy in a Large Prospective Study," *Obstetrics & Gynecology*, vol. 83, No. 1, pp. 5–11 (1994).

Herman, C. et al., "Soybean Phytoestrogen Intake and Cancer Risk," *American Institute of Nutrition*, pp. 757S–770S, (1995).

Holt, S., "Selected Bibliography of Scientific Studies on Genistein and Other Soya Isoflavones," Soya for Health: The Definitive Medical Guide, Mary Ann Liebert, Inc., Larchmont, NY, pp. 159–170, (1996).

Jenkins, D.J.A. et al., "Leguminous seeds in the dietary management of hyperlipidemia," *Am. J. Clin. Nut.*, vol. 38, pp. 567–573, (1983).

Joannou, G.E. et al., "A Urinary Profile Study of Dietary Phytoestrogens. The Identification and Mode of Metabolism of New Isoflavonoids," *J. Steroid Biochem. Molec. Biol.*, vol. 54, No. 3/4, pp. 167–184, (1995).

Jones, A.E. et al., "Development and Application of a High–performance Liquid Chromatographic Method for the Analysis of Phytoestrogens," *J. Sci. Food Agric.*, vol. 46, pp. 357–364, (1989).

Kaldas, R.S. et al., "Reproductive and General Metabolic Effects of Phytoestrogens in Mammals," *Reproductive Toxicology*, vol. 3, No. 2, pp. 81–89, (1989).

Kao, Y., et al., "Molecular Basis of the Inhibition of Human Aromatase (Estrogen Synthetase) by Flavone and Isoflavone Phytoestrogens: A Site–directed Mutagenesis Study," *Environmental Health Perspectives*, vol. 106, No. 2, pp. 85–92 (1998).

Kelly, G. et al., "Standardized Red Clover Extract Clinical Monograph," Natural Products Research Consultants, Inc., Seatle, WA, pp. 3–12, (1998).

Kitada, Y. et al., "Determination of isoflavones in soy bean by high–performance liquid chromatography with amperometric detection," *J. Chromatography*, vol. 366, pp. 403–406, (1986).

Kitts, D.D. et al., "Uterine Weight Changes and $^3$H–Uridine Uptake in Rats Treated with Phytoestrogens," *Can. J. Anim. Sci.*, vol. 60, pp. 531–534, (1980).

Knuckles, B.E. et al., "Coumestrol Content of Fractions Obtained during Wet Processing of Alfalfa," *J. Agric. Food Chem.*, vol. 24, No. 6, pp. 1177–1180, (1976).

Kudou, S. et al., "A New Isoflavone Glycoside in Soybean Seeds (*Glycine max* Merrill), Glycitein 7–O–β–D–(6"–O–Acetyl)–Glucopyranoside," *Agric. Biol. Chem.*, vol. 55, No. 3, pp. 859–860, (1991).

Kudou, S. et al., "Malonyl Isoflavone Glycosides in Soybean Seeds (*Glycine max* Merrill)," *Agric. Biol. Chem.*, vol. 55, No. 9, pp. 2227–2233, (1991).

Lindner, H.R., "Study of the Fate of Phyto–Oestrogens in the Sheep by Determination of Isoflavones and Coumestrol in the Plasma and Adipose Tissue," *Aust. J. Agric. Res.*, vol. 18, pp. 305–333, (1967).

Liu, Y. et al., "Abstract No. 78763p; Effects of solid dispersion of diadzein on the blood pressure of spontaneously hypersensitive rats," Chemical Abstracts, vol. 115, No. 8, p. 466, (1991).

Lock, M., "Contested meanings of the menopause," *The Lancet*, vol. 337, pp. 1270–1272, (1991).

Mäkelä, S., et al., "Inhibition of 17β–Hydroxysteroid Oxidoreductase by Flavonoids in Breast and Prostate Cancer Cells," pp. 310–316 (1998).

Martin, P.M. et al., "Phytoestrogen Interaction with Estrogen Receptors in Human Breast Cancer Cells," *Edocrinology*, vol. 103, No. 5, pp. 1860–1867, (1978).

Messina, M. et al., "The Role of Soy Products in Reducing Risk of Cancer," *J. of National Cancer Institute*, vol. 83, No. 8, pp. 541–546, (1991).

Morris, P., "Identification and accumulation of isoflavonoids and isoflavone glucosides in soybean leaves and hypocotyls in resistance responses to *Phytophthora megasperma* f.sp. *glycinea*," *Physiological and Molecular Plant Pathology*, vol. 39, pp. 229–244, (1991).

Mowrey, D.B., "Introduction," in *Next Generation Herbal Medicine: Guaranteed Potency Herbs*, 2$^{nd}$ Edition, Keats Publishing, Inc., New Canaan, CT, pp. 3–13, (1998).

Murphy, P.A., "Phytoestrogen Content of Processed Soybean Products," *Food Technology*, pp. 60–64, (1982).

Murphy, P.A., "Separation of genistin, daidzin and their aglucones, and coumesterol by gradient high–performance liquid chromatography," *J. Chromatography*, vol. 211, pp. 166–169, (1991).

Naim, M. et al., "A New Isoflavone from Soya Beans," *Phytochemistry*, vol. 12, pp. 169–170, (1973).

Naim, M. et al., "Soybean Isoflavones. Characterization, Determination, and Antifungal Activity," *J. Agr. Food Chem.*, vol. 22, No. 5, pp. 806–810, (1974).

Namnoum, A.B., et al., "Incidence of symptom recurrence after hysterectomy for endometriosis," *Fertility and Sterility*, vol. 64, No. 5, pp. 898–902 (1995).

Nash, A.M. et al., "Fractionation and Characterization of Alcohol Extractables Associated with Soybean Proteins. Nonprotein Components," *J. Agr. Food Chem.*, vol. 15, No. 1, pp. 102–108, (1967).

Ohta, N. et al., "Isoflavonoid Constituents of Soybeans and Isolation of a New Acetyl Daidzin," *Agric. Biol. Chem.*, vol. 43, No. 7, pp. 1415–1419, (1979).

Okano, K. et al., "Isolation of Four Kinds of Isoflavon from Soya Bean (abstract)," *Bron: Bull. Agr. Chem. Soc. Japan*, vol. 15, p. 110, (1939).

Okubo, K. et al., "Components Responsible for the Undesirable Taste of Soybean Seeds," *Biosci. Biotech. Biochem.*, vol. 56, No. 1, pp. 99–103, (1992).

Pope, G.S., "The Importance of Pasture Plant Oestrogens in the Reproduction and Lactation of Grazing Animals," *Dairy Science Abstracts*, vol. 16, No. 5, pp. 333–356, (1954).

Price, K.R. et al., "Naturally occurring oestrogens in foods—A review," *Food Additives and Contaminants*, vol. 2, No. 2, pp. 73–106, (1985).

Peterson, G. et al., "Genistein and Biochanin A Inhibit the Growth of Human Prostate Cancer Cells but not Epidermal Growth Factor Receptor Tyrosine Autophosphorylation," *The Prostate*, vol. 22, pp. 335–345, (1993).

Peterson, G. et al., "Genistein Inhibition of the Growth of Human Breast Cancer Cells: Independence From Estrogen Receptors and the Multi–drug Resistance Gene," *Biochemical and Biophysical Research Communications*, vol. 179, No. 1, pp. 661–667, (1991).

Reinli, K. et al., "Phytoestrogen Content of Foods—A Compendium of Literature Values," *Nutrition and Cancer*, vol. 26, No. 2, pp. 123–148, (1996).

Rose, D.P., "Dietary Fiber, Phytoestrogens, and Breast Cancer," *Nutrition*, vol. 8, No. 1, pp. 47–51, (1992).

Rossiter, R.C., "Physiological and Ecological Studies on the Oestrogenic Isoflavones in Subterranean Clover (*T. subterraneum* L.), III: Effects of Light" *Aust. J. Agric. Res.*, vol. 18, No. 1, 23–37, (1967).

Rossiter, R.C., "Physiological and Ecological Studies on the Oestrogenic Isoflavones in Subterranean Clover (*T. subterraneum* L.), IV: Effects of Zinc Deficiency in Clover Seedlings," *Aust. J. Agric. Res.*, vol. 18, No. 1, 39–46, (1967).

Sanchez–Guerrero, J. et al., "Postmenopausal Estrogen Therapy and the Risk for Developing Systemic Lupus Erythematosus," *Annals of Internal Medicine*, vol. 122, No. 6, pp. 430–433 (1995).

Sener, A.B., et al., "The effects of hormone replacement therapy on uterine fibroids in postmenopausal women," *Fertility and Sterility*, vol. 65, No. 2, pp. 354–357 (1996).

Seo, A. et al., "Improved High–Performance Liquid Chromatographic Analysis of Phenolic Acids and Isoflavonoids from Soybean Protein Products," *J. Agric. Food Chem.*, vol. 32, No. 3, pp. 530–533, (1984).

Setchell, K.D.R. et al., "High–Performance Liquid Chromatographic Analysis of Phytoestrogens in Soy Protein Preparations with Ultraviolet, Electrochemical and Thermospray Mass Spectrometric Detection," *J. Chromatography*, vol. 386 pp. 315–323, (1987).

Setchell, K.D.R. et al., "14: Mammalian Lignans and Phyto–oestrogens Recent Studies on their Formation, Metabolism and Biological Role in Health and Disease," in *Role of the Gut Flora in Toxicity and Cancer*, I.R. Rowland (Ed.), Academic Press, Inc., San Diego, CA, pp. 315–339, (1988).

Setchell, K.D.R. et al., "Nonsteroidal estrogens of dietary origin: possible roles in hormone–dependent disease," *Am. J. Clin. Nut.*, vol. 40, pp. 569–578, (1984).

Shimoyamada, M. et al., "Saponin Composition in Developing Soybean Seed (*Glycine max* (L.) Merrill, cv. Mikuriyaao)," *Agric. Biol. Chem.*, vol. 55, No. 5, pp. 1403–1405, (1991).

Shutt, Donald A., "The effects of plant oestrogens on animal reproduction," *Endeavour*, vol. 35, pp. 110–113, (1976).

Shutt, D.A. et al., "Free and Conjugated Isoflavones in the Plasma of Sheep Followed Ingestion of Oestrogenic Clover," *Aust. J. agric. Res.*, vol. 18, pp. 647–655, (1967).

Shutt, D.A., "Interaction of Genistein With Oestradiol in the Reproductive Tract of the Ovariectomized Mouse," *J. Endocrin.*, vol. 37, pp. 231–232, (1967).

Shutt, D.A. et al., "Quantitative Aspects of Phyto–Oestrogen Metabolism in Sheep Fed on Subterranean Clover (*Trifolium subterraneum* Cultivar Clare) or Red Clover (*Trifolium pratense*)," *Aust. J. agric. Res.*, vol. 21, pp. 713–722, (1970).

Shutt, D.A. et al., "The Significance of Equol in Relation to the Oestrogenic Responses in Sheep Ingesting Clover with a High Formononetin Content," *Aust. J. agric. Res.*, vol. 19, pp. 545–553, (1968).

Shutt, D.A. et al., "Steroid and Phyto–Oestrogen Binding to Sheep Uterine Receptors In Vitro," *J. Endocr.*, vol. 52, pp. 299–310, (1972).

Smith, A.K. et al. (Eds.), "Solvent Treatment of Beans and Fractions," in *Soybeans: Chemistry and Technology vol. 1: Proteins*, Avi Publishing Co., Inc., Westport, CT, p. 149, (1972).

Smith, A.K. et al. (Eds.), "Phenolic Constituents," in *Soybeans: Chemistry and Technology vol. 1: Proteins*, Avi Publishing Co., Inc., Westport, CT, pp. 187–189, (1972).

Smith, G.R. et al., "Influence of Harvest Date, Cultivar, and Sample Storage Method on Concentration of Isoflavones in Subterranean Clover," *Crop Science*, vol. 26, pp. 1013–1016, (1986).

Trease, G.E. et al., "20: Introduction and General Methods," in *Pharmacognosy, 12$^{th}$ edition*, Bailliére Tindall, Alden Press, Oxford, Great Britain, pp. 241–260, (1983).

Troisi, R.J., et al., "Menopause, Postmenopausal Estrogen Preparations and the Risk of Adult–Onset Asthma," *Am J Respir Crit Care Med*, vol. 152, pp. 1183–1188 (1995).

Verdeal, Kathey et al., "Naturally–Occurring Estrogens in Plant Foodstuffs—A Review," *J. Food Protect.*, vol. 42, No. 7, pp. 577–583 (1979).

Walter, E.D., "Genistin (an Isoflavone Glucoside) and its Aglucone, Genistein, from Soybeans," *J. Am. Chem. Soc.*, vol. 63, p. 3273, (1941).

Wang, C., et al., "Phytoestrogen Concentration Determines Effects on DNA Synthesis in Human Breast Cancer Cells," *Nutrition and Cancer*, 28(3), pp. 236–247, (1997).

Wang, G. et al., "A Simplified HPLC Method for Determination of Phytoestrogens in Soybean and Its Processed Products," *J. Agric. Food Chem.*, vol. 38, No. 1, pp. 185–190 (1990).

Welshons, W.V. et al., "Stimulation of breast cancer cells in vitro by the environment estrogen enterlactone and the phytoestrogen equol," *Breast Cancer Research and Treatment*, vol. 10, 169–175, (1987).

White, E. et al., "Extracta," in *Pharmacopedia; A Commentary on the British Pharmacopoeia, 1898, 2$^{nd}$ Edition*, Simpkin, Marshall, Hamilton, Kent & Co., Ltd., London, England, pp. 166–167, (1909).

Wilcox, G. et al., "Oestrogenic effects of plant foods in postmenopausal women," *British Med. J.*, vol. 301, pp. 905–906, (1990).

Wong, E., "Detection and Estimation of Oestrogenic Constituents in Red Clover," *J. Sci. Food Agric.*, vol. 13, pp. 304–308, (1962).

Wong, E. et al., "The Oestrogenic Activity of Red Clover Isoflavones and some of Their Degradation Products," *J. Endocrin.*, vol. 24, pp. 341–348, (1962).

\* cited by examiner

THERAPY OF ESTROGEN-ASSOCIATED DISORDERS

This is a National Stage application under 35 U.S.C. §371 of PCT Application No. AU99/00222, filed Mar. 26, 1999, corresponding to Australian Patent Application No. PP 2607, filed Mar. 26, 1998.

This invention relates to methods and compositions for the treatment, prophylaxis, amelioration or prevention of disorders associated with abnormally high activity of steroidal estrogens, using a plant extract enriched for estrogenic isoflavones preferably comprising predominantly biochanin or a high ratio of biochanin to a mixture of other estrogenic isoflavones comprising formononetin, daidzein and genistein. The targeted conditions specifically include uterine fibroids, polycystic ovarian disease, ovarian cysts, mastalgia, cyclical acne, endometriosis and endometrial hyperplasia.

The aforementioned conditions usually are considered as a group because of a number of common characteristics. They occur almost exclusively in pre-menopausal women and therefore are thought to be associated with high blood levels of steroidal sex hormones, and they are associated with benign, hyperplastic and proliferative changes in the tissues of the is female reproductive tract (with the exception of cyclical acne).

The prominent role of steroidal estrogen in thee conditions is suggested by the observations firstly that these conditions and symptoms occur almost predominantly in pre-menopausal women and usually disappear with the onset of menopause, secondly, they often get worse during the mid-phase of the menstrual cycle when cyclical estrogen levels are highest, they usually are exacerbated by the use of steroidal estrogen therapy, and lastly they usually respond to therapies such as GnrH agonists, oral contraception, or oophorectomy, all of which have the effect of reducing steroidal estrogen production in the body.

Uterine fibroids are a particularly common problem with more than 30% of women developing fibroids by the time they reach menopause. Fibroids are benign adenomas originating in the uterine wall and composed of fibrous tissue. For some women, the fibroids can be small and essentially asymptomatic. For other women, the fibroids can be of such a size to cause symptoms such as severe menstrual bleeding and uterine cramping (with fibroids that disrupt the endometrium) or constipation and urinary frequency (with large, space-occupying fibroids that grow out into the pelvic cavity). Estrogen therapy is known to aggravate fibroids and the symptoms associated with fibroids [Grodstein et al. "Postmenopausal hormone use and colecystectomy in a large prospective study." *Obstetrics and Gynaecology*: 1994: 83(1), 5–11; Akkad et al. "Abnormal uterine bleeding on HRT: The importance of intrauterine structural abnormalities." *Obstetrics and Gynaecology*, 1995. 86(3): 330–334; Sener et al. "The effects of HRT on uterine fibroids in postmenopausal women." *Fertility and Sterility*, 1996. 65(2): 354–3571]. The usual treatment for fibroids is surgical removal (hysterectomy or hysterotomy).

Endometrial hyperplasia is thought to affect between 5–15% of pre-menopausal women. It involves an abnormal thickening of the endometrium that is not completely shed at the time of menstruation. The symptoms can include painful and heavy menstruation, and painful sexual intercourse. Treatment usually consists of surgery (curettage or hysterectomy).

Endometriosis affects about 5% of pre-menopausal women. This condition is due to the appearance of endometrium in the peritoneal cavity. Patches of endometrium can grow on the serosal surface of the ovaries, uterus, bladder, large intestine or the peritoneum. These patches respond to normal hormonal changes over the menstrual cycle in parallel to that of the endometrium the uterus and can bleed, swell and cause severe pelvic discomfort and pain. Standard therapy of endometriosis is surgical ablation of the abnormal tissue, although the recurrence rate is high, requiring ongoing surgical treatment [Namnoum et al. "Incidence of symptom recurrence after hysterectomy for endometriosis." *Fertility and Sterility*, 1995. 64(5): 898–902]. Endometriosis also is aggravated by estrogen therapy [Goh et al. "Postmenopausal endometrioma and HRT" *Australia New Zealand of Obstetrics and Gynaecology*, 1992. 32(4): 384–385].

Ovarian cysts are thought to affect up to about 20% of pre-menopausal women. The pathology is that of multiple, incomplete follicles within the body of the ovary. A variant of this condition is known as polycystic ovarian disease which is characterised by excessive androgen production from the follicles stimulated by abnormally high insulin levels. Excess androgens are often converted to steroidal estrogen. The usual symptoms of polycystic ovarian disease are hirsutism and acne. The normal treatment for these conditions are GnrH agonists that function by down-regulating the release of gonadotrophins (FSH and LH) from the hypothalamus, thereby inhibiting and further ovulation.

Mastalgia is also known as cyclical mastalgia or fibrocystic breast disease. It is characterised by the retention of fluid in cysts within the fibrous tissue of the breast. It normally is associated with swelling, pain and tenderness, with symptoms usually worsening about the middle of the menstrual cycle when estradiol levels peak in the blood. No effective therapy for this condition is known.

Cyclical acne normally is restricted to post-adolescent women. It is associated with severe acne over the face and upper torso and normally the acne worsens on a cyclical basis in parallel with the menstrual cycle. The normal therapy for this condition is oral contraception in order to regulate ovulation and estrogen production.

In general, the management of these aforementioned conditions is unsatisfactory. Surgery is the most common method of treatment, and apart from the dramatic and intrusive nature of this approach, an inevitable outcome often is sterility as a result of removal of ovaries and/or uterus. The use of GnrH agonists also is not without adverse consequences as it invariably leads to premature menopause, with its attendant increased risks of osteoporosis and heart disease.

The underlying causes of or risk factors for the aforementioned conditions are unknown. Genetic risk factors are not reported, neither are lifestyle risk factors. There is no reliable epidemiological data reported that links the incidence of any one of these conditions or the group of conditions as a whole to specific communities or racial groups, or to lifestyle factors such as diet. However, it generally is recognised that the conditions or symptoms are associated with excess estrogen stimulation of tissues of the female reproductive tract and that it would be prudent to avoid any situation likely to aggravate estrogenic activity.

Plant estrogens including estrogenic isoflavones recently have come to medical attention because they mimic the effect/activity of steroidal estrogens and their biologically active analogues by binding to and activating estrogen receptors on animals (including human) cells. Plant isoflavones such as formononetin, biochanin, daidzein and genistein are known to be estrogenic in vitro, acting as agonists for the human estrogen receptor. Their ability to function as estrogens in the body is well understood and the epidemiological link between diets high in these estrogenic isoflavones and low incidences of certain estrogeneficiency states also is well documented. This has led to considerable interest in the use of dietary estrogens such as isoflavones to provide a supplementary estrogenic activity in menopausal women, providing relief from estrogen-deficiency symptoms including hot flushes, mood swings, osteoporosis, hypertension, and hypercholesterolaemia.

Given the current understanding about the estrogenic action of isoflavones, and the adverse consequences of estrogen therapy on the aforementioned pre-menopausal conditions and symptoms, estrogenic isoflavones would appear to be contra-indicated for subjects suffering from those conditions or symptoms. While the incidences of these conditions are adequately reported in women in Western countries where the diet is low in dietary isoflavones, there is no known data on the incidences in communities that typically ingest high levels of estrogenic isoflavones. It would be reasonable, however, to assume that it would particularly contra-indicated for pre-menopausal women at risk of the aforementioned conditions and symptoms to extensively consume foodstuffs such as clover that is the richest source of estrogenic isoflavones in nature. Therefore, the applicants were surprised to find that isoflavone-containing extracts of clover or chickpeas were particularly beneficial in the treatment of estrogen-sensitive conditions.

Clovers (Trifolium spp.) are one of the richest sources of estrogenic isoflavones in the plant kingdom, with some cultivars containing up to 5% of their dry weight as estrogenic isoflavones. The use of subterranean clovers in agriculture is associated with a condition in sheep known as 'clover disease'. This disease is due to excessive ingestion of estrogenic isoflavones resulting in hyperplastic changes in the lower reproductive tract. The linings of the uterus, cervix and vagina of sheep undergo dramatic proliferative changes and the ovaries show multiple cyst formation, all of which produces temporary and then permanent infertility. The pathology of these changes in sheep closely parallels that in humans with conditions such as endometaial hyperplasia. The likelood that estrogenic isoflavones might exacerbate such conditions in women, particularly in those women with little prior exposure to isoflavones, is therefore is a real concern.

Clovers such as red clover have enjoyed some therapeutic use by herbal practitioners over the centuries for various human ailments such as asthma and eczema and have not been noted as having any association with increased incidence of reproductive disorders. It should be noted that the traditional herbal use of red clover employs the flower and this part of the plant contains very little isoflavone. Also, red clover occurs in multiple cultivars and many cultivars have very low isoflavone levels. Thus it is not possible to ascribe any putative therapeutic benefit from herbal medicinal use to their isoflavone content, and nor is it possible to ascribe any apparent lack of adverse side effects to the safety of isoflavones.

In spite of this background, the applicant surprisingly has found that clover extracts preferably those enriched for certain estrogenic isoflavones may be used in the prevention and treatment of conditions of the female reproductive tract associated with excessive estrogen activity. Even more surprising is the finding that a particular ratio of different types of estrogenic isoflavones in the extract is primarily responsible for the demonstrated therapeutic effects. Preferably the extract comprises biochanin as the principal isoflavone. In the context of this invention, it has been found that the preferred ratio of biochanin to the other three main estrogenic isoflavones embraces the various naturally-occurring forms of isoflavones including their aglycone, glycoside, acetyl or malonyl forms.

In accordance with a first aspect of this invention there is provided a method for the treatment, prophylaxis, amelioration or prevention of disorders associated with an abnormally high activity of steroidal estrogen, which includes administering to a human subject a composition comprising an isoflavone containing extract of clover or chick pea, or an isoflavone extract of clover or chick pea comprising primarily biochanin or biochanin and any one or more of the isoflavones from the group formononetin, daidzein and genistein at a ratio from about 2:1 to about 5:1, optionally in association with one or more pharmaceutically acceptable carriers, excipients, auxiliaries and/or diluents.

Preferably the disorder is selected from uterine fibroids, polycystic ovarian disease, ovarian cysts, cyclical acne, mastalgia, endometriosis and endometrial hyperplasia.

By reference to an extract comprising "primarily biochanin" is meant a biochanin content of at least 65% by weight isoflavone cot, such as 70 to 100%, more preferably 75 to 90% biochanin, the remainder of isoflavone content comprising essentially formononetin, daidzein and genistein.

The high ratio of biochanin to the other three estrogenic isoflavones in the range from about 2:1 to about 5:1 is responsible for the optimal unexpected therapeutic effects according to this invention. Outside of this range of ratios, the therapeutic benefits effectively are not observed, or if observed are considerably less effective. The ratio of biochanin to the other three isoflavones may, for example, be from about 7:3 to about 5:1.

In a further aspect of this invention there is provided a composition comprising an isoflavone-rich extract from clover or chick pea, said extract comprising a ratio of biochanin to formononetin, daidzein and genistein at a ratio from about 2:1 to about 5:1, optionally in association with one or more pharmaceutically acceptable carriers, excipients, auxiliaries, and/or diluents.

In a further aspect of the invention there is provided use of a composition comprising an isoflavone extract of clover or chick pea, said extract comprising primarily biochanin, or a ratio of biochanin to formonemn, daidzein and genistein at a ratio of from about 2:1 to about 5:1, optionally in association with one or more pharmaceutically acceptable carriers, excipients, auxiliaries, and/or filaments for the manufacture of a medicament for the treatment, prophylaxis, amelioration or prevention of disorders associated with an abnormally high activity of steroidal estrogen.

Scientific interest in isoflavones up until now has focused on daidzein and genistein. This is in part because of the belief that these two isoflavones are the most prominent in the human diet. But mainly it is because of the general belief that formononetin and biochanin are unlikely to have any biological significance in their own right. Formononetin and biochanin are mentholated versions of daidzein and genistein respectively and it is thought that humans have the capacity to convert formononetin to daidzein and biochanin to genistein. In sheep, the only animal species in which isoflavone metabolism has been extensively studied, this conversion is virtually 100% effective. Sheep consume predominantly formononetin and biochanin as a result of eating isoflavone-rich clovers, with virtually all formononetin being demethylated to daidzein and all biochanin being demethylated to genistein. Reports of analyses of blood or urine of humans ingesting diets rich in isoflavones has failed to demonstrate any formononetin and biochanin as being present, leading to the general assumption that the same situation applies in humans. That is, even if formononetin and biochanin are present in the diet, there is a general assumption that they are converted to daidzein and genistein and that it is these two isoflavones that hold the true source of biological significance to humans. The dominant use of soya as a source of dietary isoflavones by the health food and pharmaceutical industries is testament to this, with soya containing predominantly daidzein and genistein (95–99%) and only trace amounts of biochanin and formononetin.

The inventors were therefore very surprised to find that an extract of red clover or chick peas, preferably enriched for or comprising biochanin as the principal isoflavone, provided a therapeutic effect quite distinct from that seen with the same dose of isoflavones containing predominantly daidzein and genistein. This suggests that biochanin provides a distinctive and individualistic biological effect.

It has been recognized for some time that the four estrogenic isoflavones have an individual biological profile. That is, genistein is approximately ten fold more estrogenic than daidzein, and genistein has potent anti-cancer actions while daidzein has virtually none. The finding that biochanin might therefore also have a distinctive biological profile is not surprising, but that it should be able to maintain this distinction when its presence in the human body has not previously been demonstrated is surprising.

This finding was even more surprising given what generally is known about the action of isoflavones at the cellular level and the manner in which they function as estrogens. Compounds can exert an estrogenic effect in the body in one of two ways, either indirectly, by stimulating the brain to produce gonadotropins that in turn cause the body to make more estradiol, or directly, by attaching to and activating the human estrogen receptor (hER). The isoflavones are thought to act directly in the same way as the steroidal estrogen, estradiol, and some evidence exists to support that belief. Recent studies, however, point to isoflavones having an important difference to that of estradiol in the way they art as estrogens. Two distinct types of hER now have been identified, known as alpha-ER and beta-ER. Whereas estradiol binds with similar strengths to both ER types and appears to be able to stimulate both receptor types equally, the isoflavonoids are quite different. They show significantly greater agonism to the beta-ER than to the alpha-ER. The significance of this phenomenon lies in the fact that alpha-ER dominates on tissues of the female reproductive tract (vagina, endometrium, breast, ovary), while beta-ER dominates on most other tissues (brain, bone, endothelium etc.). The fact that isoflavones have weak affinity for alpha-ER is confirmed by clinical studies and epidemiological observations that diets rich in estrogenic isoflavones have little or no stimulatory effect on female reproductive tissue in postmenopausal women. But the experience with 'Clover Disease' in sheep teaches us that this most likely is a dose-related effect—if sufficient isoflavones are ingested, then it is possible to achieve stimulation of the alpha-ER, producing proliferation of the reproductive tissues. Importantly, however, at normal dietary dosages, estrogenic isoflavones appear to have little or no impact on tissues expressing mainly alpha-ER.

Without wishing to be bound by any particular theory of action, there are multiple possible is mechanisms by which biochanin may be providing a therapeutic benefit in reducing the impact of steroidal estrogens on the reproductive tissues. One likely explanation is the way in which biochanin interacts with the alpha-ER, but this again is surprising given that there is no known difference in the way in which any of the four estrogenic isoflavones behave as ligands with this receptor.

It has been theorised that one of the biological effects of isoflavones is their ability to 'competitively inhibit' the action of steroidal estrogens such as estradiol. By this process, the isoflavonoid, being a weaker estrogen, once bound to the hER and occupying the receptor site, prevents the more estrogenic estradiol reaching the receptor. Isoflavones are weak estrogens, having an estrogenic potency between about 1:250 to 1:2,000 that of estradiol, and while they have considerably lower affinity for the hER compared to estradiol, the substantially greater numbers of isoflavones in the blood relative to estradiol means that a significant proportion of hER will be occupied by isoflavones. This theory holds that even though the isoflavonoid produces a weak estrogenic response, the fact that it has prevented a more potent response by estradiol means that the net effect has been one of a reduced estrogenic effect. This theory could be used to explain the ability of isoflavones to reduce the impact of estradiol on the female reproductive tissues during the pre-menopausal years when estradiol levels are at their highest.

Biochanin has about the same estrogenic potency as daidzein and there is some evidence that it has lower binding affinity for the hER compared to daidzein. Therefore even if competitive-inhibition is a contributing factor the clinical observation by the inventors, then it is even more surprising that an extract principally comprising biochanin should be more efficacious than an extract principally comprising daidzein and genistein.

Preferably the extract of clover is prepared by a water/water-miscible organic solvent extract of clover. The ratio of water to water-miscible organic solvent is generally in the range of 1:10 to 10:1 and may for example comprise equal proportions of water and solvent or from 1% to 30% (v/v) water-miscible organic solvent. Any water-miscible organic solvent or a mixture of such solvents may be used. The water-miscible organic solvent is preferably a C2–10, more preferably C1–4 water-miscible organic solvent (such as methanol, ethanol, propanol, propylene glycol, erythrite, butanol, butanediol, acetonitrile, ethyleneglycol, ethylacetate, glycidol, glycerol dihydroxyacetone or acetone). The extract in this regard is prepared by exposing the plant material to the water/water-miscible solvent mix. Optionally the mire may include an enzyme, which cleaves isoflavone glycosides to the aglucone form. The mixture may be vigorously agitated so as to form an emulsion. The temperature of the mix may range, for example, from an ambient temperature to boiling temperature. Exposure time may be between one hour to several weeks. One convenient extraction period is twenty-four hours at 90° C. The extract is separated from undissolved plant material and the water-miscible organic solvent removed, such as by distillation, rotary evaporation or other standard procedures for solvent removal. The resultant extract containing water-soluble and non-water soluble components may be dried to give an isoflavone containing extract, which may be formulated with one or more pharmaceutically acceptable carriers, excipients and/or auxiliaries. The extract following distillation contains a small amount of oil which includes isoflavones in their aglucone form (referred to herein as isoflavones). This isoflavone-enriched oil, which may be dried, for example in the presence of silica, may be formulated with one or more carriers, excipients and/or auxiliaries to give an isoflavone containing extract. Alternatively, isoflavones may be further concentrated by addition to the oil of a non-water soluble organic solvent such as hexane, heptane or octane having high solubility for oils but low solubility for isoflavones. The oil readily partitions into the organic solvent, and an enriched isoflavone containing extract falls out of solution. The recovered extract may be dried, for example in an oven at 50° C. to about 120° C., and formulated with one or more pharmaceutically acceptable carriers, excipients and/or auxiliaries.

The clover (Trifolium spp.) may be red clover (*T. pratense*), subterranean clover (*T. subterranean*), white clover (*T. repens*), or any clover related species, or chick pea variety. Preferably the clover is red clover (*T. pratense*) or subterranean clover (*T. subterranean*).

The compositions according to the present invention may include one or more pharmaceutically acceptable carriers. Carriers are selected so as to be acceptable in the sense of being ingredients in the composition and must not be deleterious to the patient. The carriers may be solid or a liquid, or both, and may be formulated with the extract as a unit-dose, for example a tablet, which may contain from 0.5% to 80% by weight of extract or up to 100% by weight to extract. Compositions may be prepared by any of the well known techniques of pharmacy, for example admixing the extract, optionally including excipients, diluents (for example water) and auxiliaries as are well known in the pharmaceutical field.

The compositions according to the invention may include one or more agents, such as vitamins (for example, Vitamin A, Vitamin B group, Vitamin C, Vitamin D, Vitamin E and Vitamin K), and minerals (for example, magnesium, iron, zinc, calcium and manganese in the form of pharmaceutically acceptable salts).

The compositions of the invention include those suitable for oral, rectal, optical, buccal (for example sublingual), parental (for example subcutaneous, intramuscular, intradermal and intravenous) and transcermal administration. The most suitable route in any given case will depend on the nature and severity of the condition being treated and the state of the patient.

Compositions suitable for oral administration may be presented in discrete units, such as capsules, cachets, lozenges, or tablets, each containing a predetermined amount of the extract; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the active compound, and one or more suitable carriers (which may contain one or more accessory ingredients as noted above). In general the compositions of the invention are prepared by uniformly and intimately admixing the extract with a liquid or finely divided solid carrier, or both, and then, if necessary, shaping the resulting mixture. For example, a tablet may be prepared by comprising or moulding a powder or granules containing the extract, optionally with one or more accessory ingredients. Compressed tables may be prepared by compressing in a suitable machine, the extracts in the form of a powder or granules optionally mixed with a binder, lubricant, inert diluents, and/or surface active/dispersing agent(s). Moulded tablets may be made by moulding, in a suitable machine, the powdered compound moistened with an inert liquid binder.

Suitable carriers may be fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylceuflose and/or polyvinylpyrrolidone, and, if desired, disintegrators, such as the above-mentioned starches, also carboxymethyl starch, cross linked polyvinyl pyrrolidone, agar or alginic acid or a salt thereof, such as sodium alginate. Excipients may be flow conditioners and lubricants, for example silicic acid, talc, stearic acid or salts thereof, such as magnesium or calcium stearate, and/or polyethylene glycol. Dragee cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragee coatings, for example for identification purposes or to indicate different doses of active ingredients.

Other orally administrable pharmaceutical compositions are dry-filled capsules made, for example, of gelatin, and soft, sealed capsules made of gelatin and a plasticiser, such as glycerol or sorbitol. The dry-filled capsules may comprise the extracts in the form of granules, for example in admixture with fillers, such as lactose, binders, such as starches, and/or glicants, such as talc or magnesium stearate, and, where appropriate, stabilisers. In soft capsules, the extract is preferably dissolved or suspended in suitable liquids, such as fatty oils, paraffin oil or liquid polyethylene glycols, to which stabilisers may also be added.

Formulations suitable for buccal (sublingual) administration include lozenges comprising the extracts in a flavoured base, usually sucrose and acacia or tragacanth; and pastilles comprising the compound in an inert base such as gelatin and glycerin or sucrose and acacia.

Compositions of the present invention suitable for parenteral administration conveniently comprise sterile aqueous preparations of the extracts, which preparations are preferably isotonic with the blood of the intended recipient. These preparations are preferably administered intravenously, although administration may also be effected by means of subcutaneous, intramuscular, or intradermal injection. Suitable compositions include water soluble extracts and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions comprising viscosity-increasing substances, for example sodium carboxymethylcellulose, sorbitol and/or dextran, and, where appropriate, also stabilisers. As an example compositions may conveniently be prepared by admixing the extracts with water or a glycine buffer and rendering the resulting solution sterile and isotonic with the blood. Injectable formulations according to the invention may contain from 0.1% to 60% w/v of the extract and may, for example, be administered at a rate of 0.1 ml/minute/kg.

Formulations suitable for rectal administration are preferably presented as unit dose suppositories. These may be prepared by admixing the extracts with one or more conventional solid carriers, for example cocoa butter, and then shaping the resulting mixture.

Compositions suitable for topical administration to the skin preferably take the form of an ointment, cream, lotion, paste, gel, spray, aerosol, or oil. Carriers which may be used include petroleum jelly, lanoline, polyethylene glycols, alcohols, and a combination of two or more thereof.

The extract is generally present at a concentration of from 0.1% to 30% weight/weight, for example from 0.5% to 10% weight/weight. The isoflavone ratio in the composition is preferably in the range of biochanin:formononetin from 2:1 to 8:1. Small or trace amounts of daidzein and biochanin may be present.

Compositions suitable for transdermal administration may be presented as discrete patches adapted to remain in intimate contact with the epidermis of the recipient for a prolonged period of time. Such patches may contain the extracts in an optionally buffered aqueous solution.

Compositions suitable for transdermal administration may also be delivered by iontophoresis (see, for example, Pharmaceutical Research 3 (6), 318 (1986)) and typically take the form of an optionally buffered aqueous solution of the extracts. Such compositions may, for example, contain citrate or bis/tris buffer (pH 6) or ethanol/water, with for example 0.05% to 30% w/w extract.

Compositions may be prepared in a manner, and in a form/amount as is conventionally practised. See for example, Goodman & Gilllan, The Pharmalogical Basis of Therapeutics (7th Edition, 1985) and Remington's Pharmaceutical Science (Mack Publishing Company, 10th Edition), both of which are incorporated herein by reference. Compositions ;nay contain, for example, from 0.1 mg to 2 g extract, such as 0.1 mg to 200 mg.

The extracts may be in the form of a powder, a slurry, in aqueous solution (for example containing a small amount of oil), particulate form, or dissolved in an organic solvent (such as methanol, ethanol, ethylacetate or dimethyl sulphoxide).

What constitutes an effective amount of the compositions of the present invention will depend upon a number of factors, such as specific mode of administration, the condition being treated, the condition of the patient and the judgment of the health care giver. Examples of dosages of extracts are about 0.1 mg to about 200 mg per day, such as in the order of 1.5 mg/kg (body weight)/day.

Preferably the extract comprises biochanin as the principal isoflavone. In the context of this invention, it has been found that the preferred ratio of biochanin to the other three main estrogenic isoflavones embraces the various naturally-occurring forms of isoflavones including their aglycone, glycoside, acetyl or malonyl forms.

This invention will now be described with reference to the following non-limiting examples.

EXAMPLE 1

A cultivar of red clover specially selected for its high biochanin content (85% biochanin, 10% formononetin, 2.5% daidzein and 2.5% genistein) is harvested and snap-frozen within 4 hours by exposure to liquid nitrogen. The material can be stored in this form for up to several years. For extraction, the frozen material is crushed to a fine powder, thawed and placed in a fine gauze bag, which is immersed in a solution of 60% ethanol in water. Extraction is carried out at 90° C. for 24 hours. The supernatant is separated from the undissolved plant material, and the solvent removed by distillation. The aqueous phase containing isoflavones in an aglucone form is extracted with an organic solvent (either petroleum ether or hexane or acetyl acetate) to remove oils and other polar compounds. The solvent then is removed by distillation and the aqueous phase taken to near-dryness by rotary evaporation. The tar-like residue then is oven-dried. The final powder typically contains 40–50% isoflavones in the ratio of biochanin:formononetin, daidzein and genistein of 5:1.

The ratio of biochanin to formononetin, daidzein and genistein may be adjusted from about 2:1 to 5:1. At this ratio the unexpected therapeutic effects of the invention are observed. The biochanin to formononetin, daidzein and genistein can be easily adjusted by HPLC fractionation of the Example 1 material, extracting a red clover cultivar comprising the appropriate ratio of components (ie. from 2:1–5:1 biochanin to formononetin, daidzein and genistein), or by adjusting the concentration of the extracting organic solvent (less organic solvent less extracted biochanin).

EXAMPLE 2

The plasma and urinary profiles of isoflavones after acute and chronic administration of 22 mg of isoflavones (genistein 0.5 g, daidzein 0.5 mg, biochanin 26 g, and formononetin 14 mg) in fourteen subjects was analysed. The composition corresponds to the Promensil product (Registered Trade Mark, Novogen Research Pty Ltd, Australia). Venous plasma and urine were collected at intervals for 24 h after which subjects commenced taking two tablets each day for two weeks and repeated plasma samples and urine were collected for a 48 h period after the last does. Plasma and urine isoflavones were assayed by HPLC.

After acute dosing all four isoflavones appeared rapidly in plasma and reached peak levels around 6 h. Although daidzein and genistein were present in much higher concentrations than their methylated precursors, indicating a rapid demethylation of these compounds, formononetin and biochanin remained detectable in both plasma and urine at all times. This was a quite unexpected finding.

EXAMPLE 3

Pharmaceutical compositions are prepared from the extracts according to the examples above.

1. The following composition is prepared in the form of a tablet:

40–60 mg of extract from Example 1

340 mg of a standard tablet inert carrier

This composition is tableted to provide a 380–400 mg tablet.

2. The following composition is prepared in the form of a capsule:

40–60 mg of extract of Example 1 or 2

190 mg of a standard pharmaceutical inert carrier all contained in a non-toxic gelatin capsule.

The carriers referred to above include cellulose (microcrystalline), calcium hydrogen phosphate, soy polysacchardie, magnesium stearate and silica-colloidal (anhydrous).

EXAMPLE 4

A 38-year old pre-menopausal woman with uterine fibroids suffered from severe and irregular menstrual bleeding. Ultrasound examination had confirmed the presence of a number of fibroids that were protruding through the endometruim. She had been taking a soy supplement delivering about 45 mg of both genistein and daidzein daily for six months with no apparent change in her symptoms. Within three months of starting treatment with red clover extract according to Example 3, her bleeding and menstrual pain became much less severe and her menstruation returned essentially to normal. An ultrasound confirmed that the fibroids had significantly reduced in size.

EXAMPLE 5

A 36-year old pre-menopausal woman had suffered endometriosis for over 5 years with progressive worsening.

A laparosoopic examination had confirmed the presence of extensive endometriosis lesions over her ovaries and serosal surface of the uterus. For 1 year she had tried a dietary change including eating tofu and soymilk on a regular basis, both foods known to contain high levels of daidzein and genistein. The condition continued to worsen and finally she was scheduled for surgery for laser burning of the islets of endometriosis tissue. She took a red clover extract according to Example (3) for 3 months prior to surgery. At the time of surgery her symptoms (pelvic pain) had reduced considerably, but it was decided to still proceed with the surgery. Laparoscopy failed to reveal any evidence of endometriosis lesions. She remains symptom-free 9 months later with ongoing daily treatment with the red clover extract.

EXAMPLE 6

A 44-year old woman had suffered ovarian cysts for 8 years, producing dysmennorhoea and low-grade pain. Various treatments including hormonal treatments had failed to improve the condition. After taking the red clover extract according to Example (3) for 3 months, her menstrual period returned to normal frequency and level of bleeding and the pain subsided. An ultrasound examination confirmed the absence of ovarian cysts on either ovary. She remains well 6 months later with no evidence of return of the cysts.

EXAMPLE 7

A 29-year old pre-menopausal woman had suffered endometrial hyperplasia for 9 years. The condition caused symptoms of heavy, frequent menstruation and menstrual cramps and pain. She had been treated periodically by curettage which had provided temporary relief only. After taking the red clover extract according to Example (3) for 4 months, her menstruation returned to normal frequency, length, duration and level of bleeding.

EXAMPLE 8

A 19-year old pre-menopausal woman suffering from severe acne and cyclical mastalgia was given the red clover extract according to Example (3) for a period of two menstrual cycles. Her pain score diary showed significant improvement for breast pain and tenderness, and a noticable improvement was seen in her acne.

EXAMPLE 9

A young woman, Mrs M, with recurrent endometriosis, and suffered severe pain and to irregular bleeding. Following daily treatment according to Example 4, her monthly pain and irregular bleeding were minimal, and prognosis for conception was improved. Improvements was seen shortly after treatment began.

Throughout this specification, unless the context requires otherwise, the word "comprise", or variations such as "comprises" or "comprising" or the term "includes" or variations thereof, will be understood to imply the inclusion of a stated element or integer or group of elements or integers but not the exclusion of any other element or integer or group of elements or integers. In this regard, in construing the claim scope, an embodiment where one or more features is added to any of claims is to be regarded as within the scope of the invention given that the essential features of the invention as claimed are included in such an embodiment.

References

1. Grodstein, F., Colditz, G. A., and Stampfer, M. J. "Postmenopausal hormone use and colecystectomy in a large prospective study" *Obstetrics and Gynaecology*: 1994: 83(1), 5–11.
2. Akkad, A. A., Habiba, M. A., Ismail, N., Abrams, K., and al-Azzawi, F. "Abnormal uterine bleeding on HRT: The importance of intrauterine strucural abnormalities" *Obstetrics and Gynaecology*, 1995. 86(3): 330–334.
3. Sener, A. G., Seckin, N. C., Ozmen, S., Gokmen, O., Dou, N. and Ekici, E. "The effects of HRT on uterine fibroids in postmenopausal women" *Fertility and Sterility*, 1996. 65(2): 354–357.
4. Namnoum, A. G., Hickman, T. N., Goodman, S. B., Gehibach, D. L., and Rock, J. A. "Incidence of symptoms recurrence after hysterectomy for endometriosis" *Fertility and Sterility*, 1995. 64(5): 898–902.
5. Goh, J. T. and Hall, B. B. "Postmenopausal endometrioma and HRT" *Australia New Zealand of Obstetrics and Gynaecology*, 1992. 32(4): 384–385.
6. Sanchez-Guerrero, J., Liang, M. H., Karlson, E. W., Hunter, D. J. and Colditz, G. A. "Postmenopausal estrogen therapy and the risk for developing systemic lupus erythematosus" *Annals of Internal Medicine* 1995. 122 (6): 430–433.
7. Troissi. R. J., Speizer, F. E., Willett, W. C., Trichopolous, D. and Rosner, B. "Menopause, postmenopausal estrogen preparations ad the risk of adult-onset asthma. A prospective cohort study" *American Journal of Respiratory and Critical Care Medicine*. 1995, 152(1), 1183–1188.

What is claimed is:

1. A method of treatment or amelioration of pre-menopausal, benign disorders associated with an abnormally high activity of steroidal estrogen, comprising administering to a human subject a composition comprising at least about 65% biochanin and at least one other isoflavone selected from formononetin, daidzein and genistein, at a ratio front about 2:1 to about 5:1.

2. A method according to claim 1 wherein the disorder is selected from uterine fibroids, polycystic ovarian disease, ovarian cysts, cyclical acne, mastalgia, endometriosis and endometrial hyperplasia.

3. A method according to claim 1 wherein the composition comprises at least about 70% biochanin.

4. A method according to claim 1 wherein the ratio of biochanin to the at least one other isoflavone is from about 7:3 to about 5:1.

5. A method according to claim 1 wherein the isoflavones are extracted from clover or chick peas by a water/water-miscible organic solvent.

6. A method according to claim 5 wherein the clover is red clover.

7. A method according to claim 1 wherein the isoflavone is in a glycoside, agylcone, acetyl or manlonyl form.

8. A method according to claim 1 wherein the composition comprises about 75% to about 90% biochanin.

9. The method according to claim 1, wherein the composition is optionally in association with one or more pharmaceutically acceptable carriers, excipients, auxiliaries and/or diluents.

* * * * *

UNITED STATES PATENT AND TRADEMARK OFFICE
CERTIFICATE OF CORRECTION

PATENT NO. : 6,599,536 B1
DATED : July 29, 2003
INVENTOR(S) : Graham Edmund Kelly and Alan James Husband It is certified that error appears in the above-identified patent and that said Letters Patent is hereby corrected as shown below:

<u>Column 12,</u>
Line 39, the word "front" should read -- from --

Signed and Sealed this

Sixteenth Day of September, 2003

JAMES E. ROGAN
*Director of the United States Patent and Trademark Office*